United States Patent [19]

Lehmer

[11] Patent Number: 4,793,345
[45] Date of Patent: Dec. 27, 1988

[54] HIGH VOLTAGE PROTECTION CIRCUIT FOR ULTRASONIC CATARACT REMOVER

[76] Inventor: Donald E. Lehmer, 687 Woodmont Ave., Berkeley, Calif. 94708

[21] Appl. No.: 65,995

[22] Filed: Jun. 24, 1987

[51] Int. Cl.$^4$ .............................................. A61B 17/39
[52] U.S. Cl. ........................... 128/303.13; 128/303.14
[58] Field of Search ............ 128/303.1, 303.13, 303.14

[56] References Cited

U.S. PATENT DOCUMENTS

| | | | |
|---|---|---|---|
| 3,699,968 | 10/1972 | Bolduc | 128/303.13 |
| 3,895,635 | 7/1975 | Justus | 128/303.13 |
| 4,122,854 | 10/1978 | Blackett | 128/303.13 |
| 4,437,464 | 3/1984 | Crow | 128/303.14 |

FOREIGN PATENT DOCUMENTS 3610393 10/1986 Fed. Rep. of Germany ........................ 128/303.13

OTHER PUBLICATIONS

1984 Linear Supplement Databook, National Semiconductor Corporation, National Semiconductor LM 1851 Ground Fault Interrupter, pp. S10-8-S10-14.

*Primary Examiner*—William L. Freeh
*Assistant Examiner*—Ted Olds
*Attorney, Agent, or Firm*—Townsend and Townsend

[57] ABSTRACT

A phacoemulsification probe for ultrasound removal of an eye lens (for example a lens having a cataract) is provided with a safety circuit for prevention of shock to the patient. The probe includes a piezoelectric sound transducer electrically powered with over 200 volts (RMS) at 50 kHz. This voltage, if improperly grounded, can be life threatening when the probe is used in the vicinity of the optic nerve. According to the improvement, the probe is provided with at least two discrete grounded paths. The power supply to the probe is enabled by a comparator testing a small current to ground through at least one and preferably both ground wires. When the existence of at least one ground path is verified and power to the probe is thus enabled, ground return from the probe flows through the paired grounded wires. This flow to ground is compared for precisely equal flows. Where non-equal flow of current to ground occurs, power to the probe is immediately interrupted. Detection of the non-equality of current flow to ground preferably occurs through a conventional toroidal current sensor electromagnetically induced by cancelling current paths within the toroid core. Where one of the paths to ground includes more than nominal resistance, as by a ground conductor being stressed, power supply trip immediately occurs. Thus, any irregularity in the required dual safety path to ground deactivates the probe and requires repair. The loss of one ground conductor terminates the application of power to the probe while still maintaining a safe ground connection through the remaining ground conductor.

3 Claims, 2 Drawing Sheets

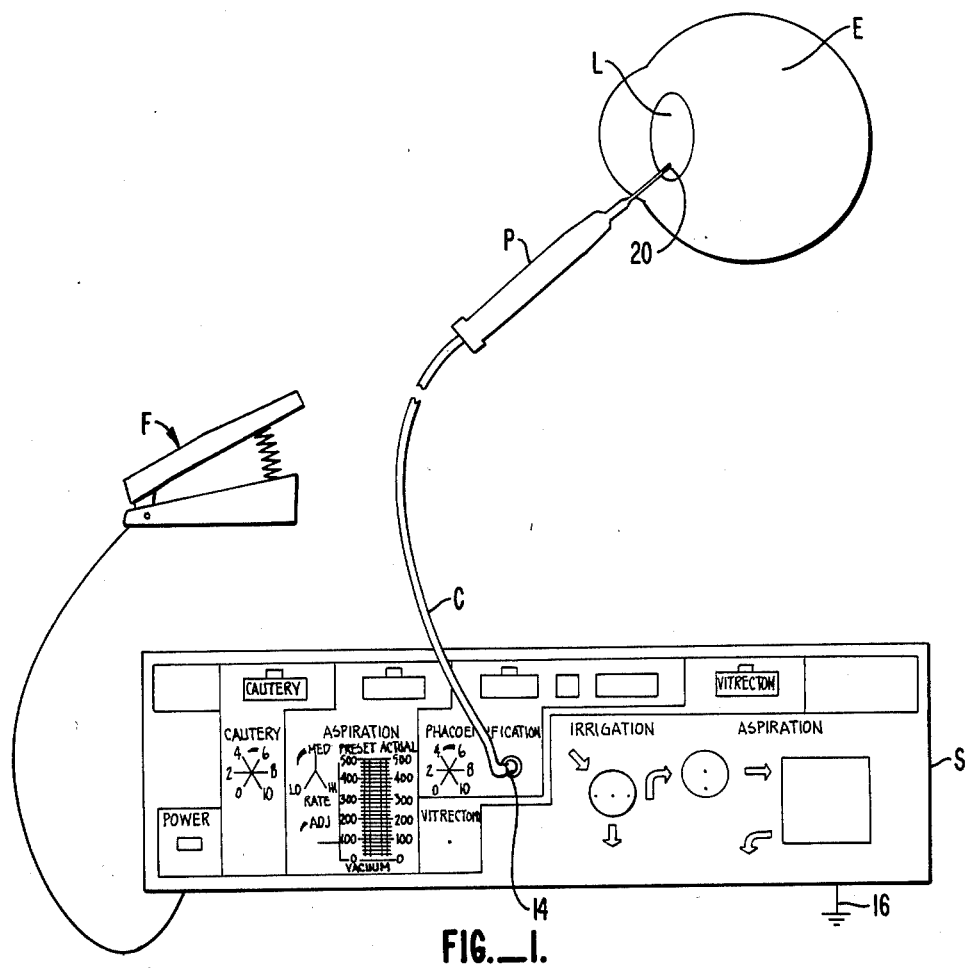
FIG._1.
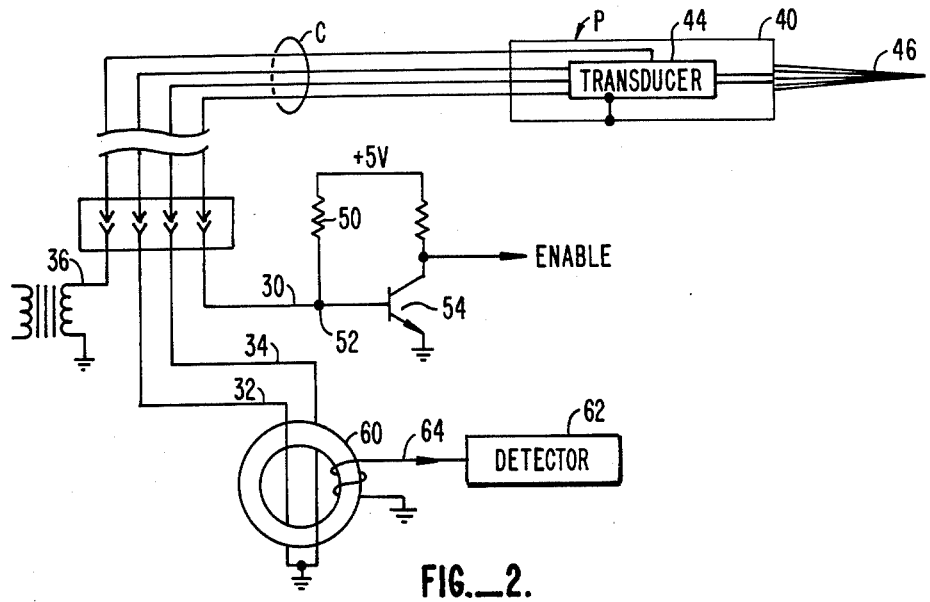
FIG._2.

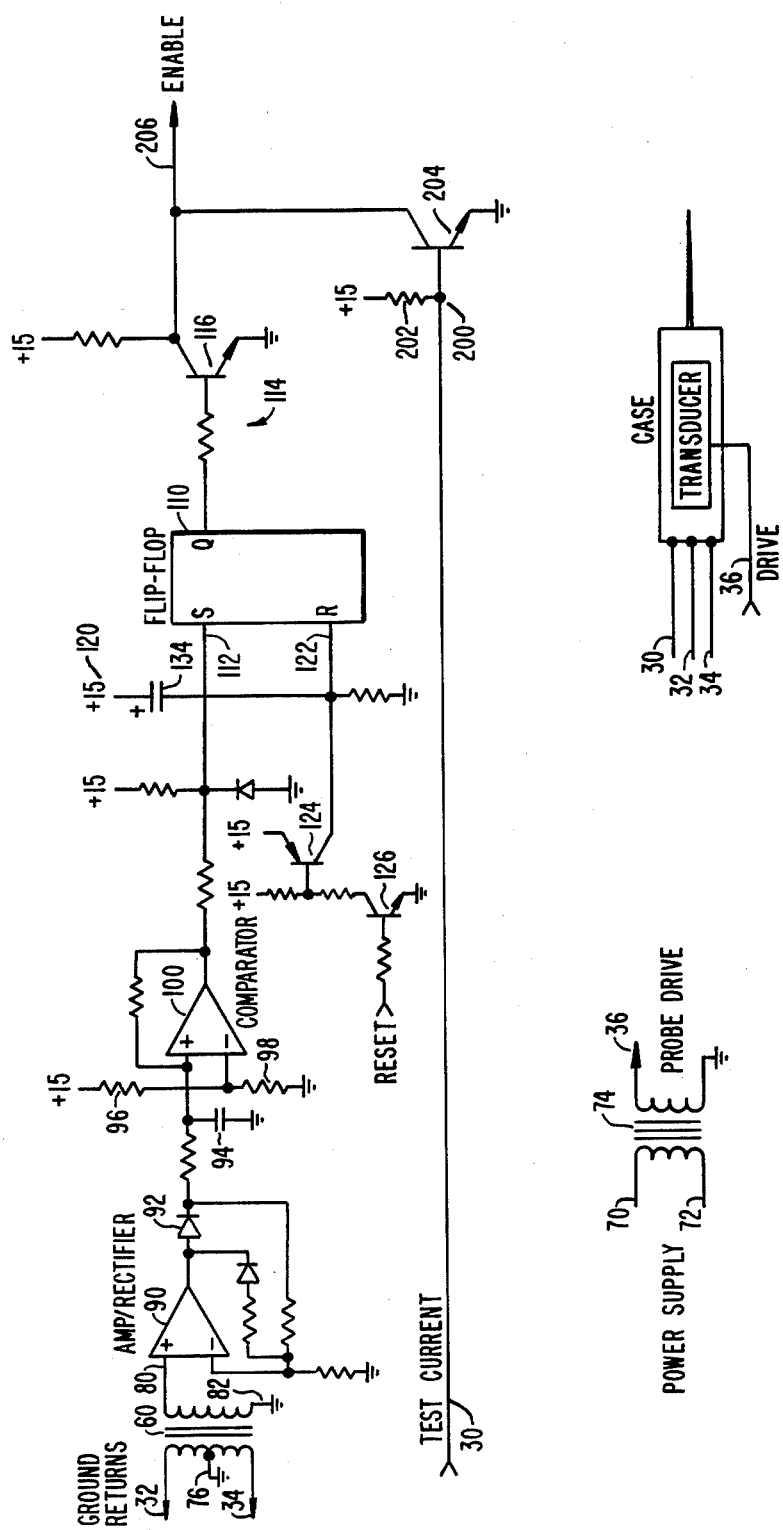
FIG._3.

HIGH VOLTAGE PROTECTION CIRCUIT FOR ULTRASONIC CATARACT REMOVER

This invention relates to a safety circuit for use in electromedical devices placing high voltage near the human body. Specifically, a high voltage protection circuit for an ultrasonic cataract remover is disclosed.

SUMMARY OF THE PRIOR ART

Ground fault interruptors are known. Typically, alternating current flow along paired conducting wires is monitored through a toroid core. A winding about the toroid core normally detects no electromagnetic force as current oscillating in one direction is precisely matched by current oscillating in the opposite direction.

Upon leakage current flowing to ground, one of the paths has a larger current component than the other path. By detecting an output from the toroidal transformer and opening an automatic switch, so-called "ground fault" protection results. The circuit immediately opens, and undesirable leakage (and possible electrocution) is prevented.

STATEMENT OF THE PROBLEM

Wires, especially high voltage wires, in the operating room environment are exposed to unusual hazards. Such wires are typically covered with silicone rubber insulation to withstand autoclaving sterilization. Silicone rubber insulation offers little strain protection for the stranded conductors. When the wire is pulled upon, the insulation offers little protection and places full strain upon the wire.

Unfortunately, such wires are frequently stressed or strained. This can occur when the probe and cable are placed in autoclave along with many other pieces of equipment. If there is any leakage in the rubber jacket, water can also attack the copper conductors and cause strand leakage. This is especially true where relatively unskilled personnel are assigned to sterilize and store the probes and cables.

The result of such dynamic strains on the cords of high voltage instruments in an operating room is deceptive. Typically, there is no discernible damage to the insulation on the outside of such wires. However, despite the absence of apparent damage, actual damage to the conducting strands on the interiors of the wires can occur. Where such damage occurs to the ground wires, a particularly hazardous condition is present.

Further, by the very nature of the damage to the wires, such interruption can be intermittent. The wires when stretched to one disposition can conduct with virtually no detectable interference. The wires when stretched to a second and different disposition—say insertion to the eye of a patient for cataract removal—can become an open circuit. To rely on defective ground wires and even a single ground wire in such an environment is not prudent.

It is important to realize that the conventional ground fault interrupter is by its very nature unsuitable for such an application. This is because the ground fault detector is used with ungrounded electrical devices where a small current to ground is taken as possibly flowing through a person. A current must flow to 'trip' the detector, the saving fact is that electrical shock of short duration is not fatal. Since the ultra-sound probe is used in the vicinity of the optic nerve the probe must be grounded to prevent any electrical shock.

SUMMARY OF THE INVENTION

A phacoemulsification probe for ultrasound removal of an eye lens (for example a lens having a cataract) is provided with a safety circuit for prevention of shock to the patient. The probe includes a piezoelectric sound transducer electrically powered with over 200 volts rms at 50 KHz. This voltage, if improperly grounded, can be life threatening when the probe is used in the vicinity of the optic nerve. According to the improvement, the probe is provided with at least two discrete grounded paths. In addition the improvement provides two separate means of determining the advisability of applying the high voltage to the probe. The first is termed the enable and the second the 'disable'. The power supply to the probe is enabled by a comparator detecting a small current to ground through at least one and preferably both ground wires. When the existence of at least one ground path is verified and power to the probe is thus enabled, the 50 kHz ground return from the probe flows through the paired grounded wires. This flow to ground is compared for precisely equal flows. Where non-equal flow of current to ground occurs, power to the probe is immediately disabled. Detection of the non-equality of current flow to ground preferably occurs through a conventional toroidal current sensor electromagnetically induced by cancelling current paths within the toroid core. Where one of the paths to ground includes more than nominal resistance, as by a ground cord being stressed, power supply trip immediately occurs. Thus, any irregularity in the required dual safety path to ground deactivates the probe and requires repair. It is important to note that the loss of one ground wire caused the power to be disabled. but the remaining ground wire maintained the electrical connection, averting electrical shock.

OTHER OBJECTS AND ADVANTAGES

An object of this invention is to disclose a safety circuit for a high voltage instrument in an operating room. According to this aspect of the invention, the high voltage instrument is provided with at least one power path and two identical ground paths. Prior to enabling the instrument, the power supply detects a small current to assure that at least one of the ground paths is operative. Upon ascertaining the operative state of the ground path, the voltage is applied to the probe, actuating the instrument. When the power path actuates the instrument, flow to ground over the plurality of ground paths (preferably two) is compared. Where resistance is precisely equal, instrument operation is allowed to continue. Where inequality of flow through the ground paths occurs, power to the instrument is disabled.

An advantage of the disclosed safety circuit is that before power is enabled, flow to ground is verified. Absent a path to ground, the instrument is completely disabled.

Yet another advantage of the instrument is that for the instrument to operate under power, two identical and intact paths to ground are required. Absent the condition of two identical and intact paths to ground, instrument operation is prevented. Since any kind of a defective path to ground requires replacement of the ultrasound probe, the possibility of electric shock is virtually eliminated.

BRIEF DESCRIPTION OF THE DRAWINGS

Other objects, features and advantages of the invention will become more apparent after referring to the following specification and attached drawings in which:

FIG. 1 is a schematic illustration of a human eye with a phacoemulsification device applied to the eye lens from a power supply with a series connected surgical foot switch being illustrated for actuating the phacoemulsification apparatus;

FIG. 2 is a schematic of the phacoemulsification probe illustrating the "enable" comparator for the power supply and the toroidal transformer for assuring equilibration in the paths ground;

FIG. 3 is a production schematic illustrating an amplifier, comparator and flip-flop for deactivating power to the high voltage probe.

Referring to FIG. 1, an operating room power supply S has a high voltage cable C connected at a standard connector 14. Cable C leads a high voltage and ground source from the supply S to a phacoemulsification probe P. Probe P and its emulsification needle 20 is shown schematically positioned to lens L of eye E.

Typically, probe P is actuated by a foot switch F used by a surgeon. It will be sufficient to say that the foot switch F is series connected to the power supply S. It will be further understood that the multiple ground path used and required by this invention extends from the probe P through the power supply S to a ground path (schematically shown at 16). The undesired and unacceptable result would be to have cable C through fault cause a (most probably) fatal path to ground through eye E, the optic nerve (not shown) in the patient.

The problem can be simply understood. The operating room is by its very nature a poor environment for high voltage conductors and their required grounds. For example, flaws can exist at the connector 14. Likewise, anywhere along the cable or at the phacoemulsification probe P bad connections can be made.

If the connection prevents power from getting to the probe, harm is not necessarily done. It is only when that power, expended at the probe cannot return through power supply S to ground 16.

Referring to FIG. 2, probe P is schematically shown. In the particular probe here illustrated, a four wire connector cable C is illustrated. The respective wire connections are the enable test conductor 30, a first ground wire 32, a second ground wire 34 and a high voltage power supply wire 36.

Probe P includes a metal handle 40, which handle is grounded by wires 32, 34. Power is supplied to a piezoelectric device 44. The piezoelectric device causes needle 46 to vibrate at the desired frequency. The vibrator causes phacoemulsification of the lens of the eye facilitating its removal.

Operation of the probe is easily understood. Specifically, when power is applied through line 36 to the piezoelectric device 44, vibration occurs. It will be understood that line 36 contains potentially fatal voltages. For example, 200 volt (RMS) at 0.2 Amps are exemplary. Such flows if grounded through the optic nerve would be immediately fatal to the patient.

Having set forth the operating environment, the function of test wire 30 will first be set forth. Thereafter, the function of ground wires 32, 34 will be discussed. It will be shown that without both wires being fully operative, operation of the phacoemulsification is completely inhibited.

Typically, conductor 30 is provided with a nonlethal test current. This current is generated by a resistor 50, connected to a positive supply. The current generated by said resistor will pass into transistor 54 base and cause said transistor to saturate in it collector circuit unless said base current is shunted to ground through either of the respective conductors 32, 34 and preferably both of the respective conductors 32, 34. The collector current of 54 will prevent the probe power supply from be enabled. The shunting of the base current via the ground return wires will prevent said collector current and allow the power supply to be enabled.

One of three cases will be observed by the transistor 54. The first case is that the current from resistor 50 will be shunted to ground through both ground return wires 32, 34. In this case the transistor 54 will be off and the power to line 36 will be enabled.

The second case is that either one of the lines 32, 34 to ground is open. If this is the case, transistor 54 will enable power to line 36.

If, however, a voltage is read at line 52, this will indicate that both paths to ground 32, 34 are open. This being the case, power to line 36 will be disabled.

It is seen immediately that without a path to ground in fact being actually read, the phacoemulsification device is disabled.

Where, however, only one of the paths to ground is operative, a potentially hazardous condition can result. If the one and remaining path to ground is for any reason disrupted, a high voltage shock condition could exist.

Continuing with the description of FIG. 2, a single turn toroid transformer 60 is schematically illustrated. It consists of a toroid core having the respective paths to ground 32, 34 pass through the toroid core in opposite directions. Assuming precisely identical resistances along the paths to ground, the magnetic flux realized at the toroid core 60 will be nonexistent.

Where, however, one leg is unbalanced with respect to the other leg (for example leg 32 having a higher impedance than leg 34), an electromotive force will be produced in the toroid core 60. This force will generate an electrical signal on conductor 64 with the same frequency as the ultrasound power supply which wil be recognized at a flux detector schematically illustrated at 62. Flux detector 62 will immediately disable power supply 36 to the phacoemulsification probe P. Replacement of the probe will be required.

Referring to FIG. 2, a schematic of the toroid transformer 60 and the respective paths 32, 34 to ground is shown. Winding of the toroidal core 60 occurs so that current flow is opposite and cancelling, presuming both conductors 32, 34 provide equal resistances in the flow to ground. Toroidal core 60 has at least one winding 64 for output to connected circuitry. Such connected circuitry can be best understood by referring to the production schematic illustrated in FIGS. 3A and 3B.

Referring to FIG. 3 supply S is illustrated having conductor 30 and transistor 204 for verifying the integrity of at least one of the ground paths 32, 34. Resistor 202 causes a small current to flow into transistor 204 base and is also connected to the case of probe P via conductor 30. This current will, in the ordinary circumstance, be returned to ground over one of the two (and preferably both) of the ground conductors 32, 34.

Where the conductors are not intact, a voltage will be present on the line 30. This voltage will appear on line 200, and turn on transistor 204, causing line 206 to go low disabling the power supply. The test for at least one ground conductor is made to prevent the supply from becoming enabled without the probe being plugged in, a dangerous "no load" condition for the power supply, and to prevent the supply from being enabled if both ground return wires are open. The reader will realize that the case of having both ground wires defective will be extremely rare; therefore the most usual case will include the circumstance where one of the two ground wires 32, 34 is defective.

The output power supply S appears on lines 70, 72, a 50 KHz sine wave for step-up to the required 200 volt (RMS) output to the probe P. This occurs through transformer 74 which typically provides step-up by a factor of 5. Transformer 60 is schematically illustrated, it being realized that between a grounded center tap 76 and the paired paths to ground 32, 34, there is only one primary winding. The secondary winding 80, 82 outputs to a detector circuit. This detector circuit includes an amplifier 90, a comparator 100 and a single stag D flip-flop 110. The function of the amplifier 90, comparator 100 and flip-flop 110 to disable drive S will now be set forth.

Amplifier 90 is an amplifier and a rectifier responsive to the positive half of the sine wave voltage detected by the secondary winding on core 60 by conductors 80, 82. Voltage is output across a diode 92 where a capacitor 94 provides a rectifier filter for detecting the peak amplifier output voltage. A voltage divider network. 96, 98, outputs to one leg of a comparator 100, forming a set point for determining an error condition. When the voltage on condenser 94 exceeds that of the set point, comparator 100 outputs a statement to flip-flop 110. Specifically. flip-flop 110 is set at input 112. Output Q1 at 114 turns on transistor 116 to ground disabling power supply S.

It will be apparent that where the circuit has detected non-equality of the ground wires 32, 34 and the probe is replaced, a reset will be required. According to this aspect of the invention, two reset methods are provided; power up reset, and front panel button reset. Power up reset occurs when the +15 volt supply 120 rises. This reset is automatically removed when condenser 134 charges about one second later. The front panel reset occurs when transistor 126 is turned on, which turns on transistor 124, causing the reset line 122 to be at a +15 volt level. This will also reset the flip-flop when the user presses a front panel switch. Once the flip-flop is reset testing for at least one ground return conductor and for equality of current flow in the paired ground connectors continues.

It should be apparent to the reader that this device is preferably used with a phacoemulsification probe. Other devices can as well be adapted to this safety circuit. Simply stated, in any high voltage device medically used in the vicinity of the human body, the scheme of dual paths to ground with initial verification of at least one path returning to ground followed by checking both paths for equality of current flow can occur.

What is claimed is:

1. In the combination of an ultrasonic cataract remover including a high voltage power source, a phacoemulsification probe for transducing power from said source to sonic energy for the phacoemulsification of the lens of the eye, a cable including a power path and a ground path for transmitting power to said probe from said power supply, and means for switching power to said cable having a first input to supply switched power to said phacoemulsification probe; the improvement in said cable and said means for switching power comprising:

said cable including first and second ground path conductors from said probe to said power supply;

said means for switching power including means for sending a small current to said probe on said power path for verifying the path to ground through at least one of said first and second ground path conductors;

means for sensing said small current at said probe having a first output operable to output a signal upon said small current at said probe;

said switching means further including a second input for disabling power to said phacoemulsification probe;

said first output from said means for sensing operatively connected to said second input to disable power to said phacoemulsification probe only upon the sensing of said switching means of a voltage at said probe;

means for comparing current flow in said paired ground wires having an output when said flow in said ground wires is other than equal; and said output from said means for comparing operatively connected to said second input of said switching means whereby said power to said phacoemulsification probe is disabled upon non-equal current flow in said ground conductors.

2. A process for testing the path to ground of a high voltage driven instrument wherein said instrument has a high voltage power source, a cable including a power path and a ground path for permitting said instrument to receive power and at least one ground path conductor for passing expended power to ground through said power supply; and a switch having a first input to supply power to said instrument; the process comprising the steps of:

providing first and second ground path conductors from said instrument to said power supply;

sending a small current on said power supply conductor for verifying the path to ground through at least one of said first and second ground path conductors;

providing in said switching means a second input for disabling power to said instrument;

sensing said small current at said probe and outputting a signal to said second input of said switching means to disable power to said instrument upon lack of a path to ground for said small test current;

operating said instrument;

during the operation of said instrument comparing current flow in said paired ground wires and outputting a signal when said current flow is other than equal; and, outputting said signal to said second input to disable power to said instrument when said flow is other than equal.

3. In combination, an instrument driven by a high voltage power source;

a high voltage power source;

a cable including a power path and two ground paths for respectively transmitting power to said instrument from said power supply an returning power to ground;

means for switching power to said cable having a first input to supply switched power to said instrument, said means for switching power including means for sending a small current to said instrument on said power path for verifying the path to ground through at least one of said first and second ground path conductors;

means for sensing said small test current at said instrument having a first output operable to output a signal upon said small test current being present at said instrument;

said switching means further including a second input for disabling power to said instrument;

said first output from said means for sensing operatively connecting to said second input of said switching means to disable power to said instrument only upon the sensing of a voltage at said instrument;

means for comparing the current flow in said paired ground wires having an output when said flow is in said ground wires is other than equal; and, said output from said means for comparing operatively connected to said second input of said switching means whereby said power to said instrument is disabled upon non-equal current flow in said ground conductors.

* * * * *